United States Patent [19]
Kumazaki et al.

[11] Patent Number: 5,568,533
[45] Date of Patent: Oct. 22, 1996

[54] K-FILTER FOR SERIAL HIGH-SPEED ROTATOGRAPHY AND APPARATUS FOR THE ROTATOGRAPHY

[75] Inventors: Tatsuo Kumazaki, 43-21, Saginomiya 4-chome, Nakano-ku, Tokyo 165; Hifumi Yamada, Tokyo, both of Japan

[73] Assignees: Tatsuo Kumazaki; Yamanouchi Pharmaceutical Co., Ltd., both of Tokyo, Japan

[21] Appl. No.: 343,488

[22] PCT Filed: May 25, 1993

[86] PCT No.: PCT/JP93/00693

§ 371 Date: Jan. 17, 1995

§ 102(e) Date: Jan. 17, 1995

[87] PCT Pub. No.: WO93/24053

PCT Pub. Date: Dec. 9, 1993

[30] Foreign Application Priority Data

| May 26, 1992 | [JP] | Japan | 4-157329 |
| Aug. 20, 1992 | [JP] | Japan | 4-242564 |
| Oct. 6, 1992 | [JP] | Japan | 4-290933 |
| Apr. 20, 1993 | [JP] | Japan | 5-115242 |

[51] Int. Cl.$^6$ ................................... A61B 6/03
[52] U.S. Cl. ............................ 378/156; 378/159
[58] Field of Search ..................... 378/156, 158, 378/159, 145, 147, 148, 150, 151

[56] References Cited

U.S. PATENT DOCUMENTS

| 3,755,672 | 8/1973 | Edholm et al. | 378/158 |
| 4,856,042 | 8/1989 | Staron et al. | 378/150 X |
| 5,148,465 | 9/1992 | Mulder et al. | 378/156 |
| 5,242,372 | 9/1993 | Carol | 378/159 X |
| 5,278,887 | 1/1994 | Chiu et al. | 378/156 |
| 5,282,254 | 1/1994 | Chiu et al. | 378/159 X |
| 5,285,489 | 2/1994 | Ohtsuchi et al. | 378/158 X |
| 5,369,678 | 11/1994 | Chiu et al. | 378/158 X |

OTHER PUBLICATIONS

JP, A, 61-142495 (Yokogawa Medical Systems, Ltd.) Jun. 30, 1986 (30. Jun. 1986), Family: none (relevant to claim No. 1).

JP, U, 2-35100 (Shimadzu Corp.), Mar. 6, 1990 (06. Mar. 1990), (Family: none) (relevant to claim No. 1).

*Primary Examiner*—David P. Porta
*Attorney, Agent, or Firm*—Sughrue, Mion, Zinn, Macpeak & Seas

[57] ABSTRACT

A K-filter is the one attached to an apparatus for serial high-speed rotatography for photographing an object to be examined by use of X-rays. The filter comprises two K-containers (5a and 5b) in which a space is defined for fluidly containing a radiopaque fluid substance, and a radiotransparent region (2) formed between the two K-containers (5a and 5b). The K-containers (5a and 5b) are pivotally supported by a supporting member (1a) and are of the inversion type which allows the radiotransparent region sides of the K-containers to move. Therefore, when this apparatus is rotated at a high speed to more than 180°, it is possible to conduct filtering under any conditions such as an inclined posture, not the horizontal posture, under which photographing is started.

47 Claims, 7 Drawing Sheets

K-FILTER FOR SERIAL HIGH-SPEED ROTATOGRAPHY AND APPARATUS FOR THE ROTATOGRAPHY

TECHNICAL FIELD

This invention relates generally to K-filters for serial high-speed rotatography and apparatus for the serial high-speed rotatography. More particularly, this invention relates to a K-filter and an apparatus for the serial high-speed rotatography which are capable of photographing radiographic images of an object speedily, accurately and with high quality from every possible angle without forming a dead angle, and hence are suitable for providing useful and detailed information to make a precision diagnosis immediately and determine a therapeutic treatment plan without delay.

BACKGROUND ART

Various photographic techniques using radiopaque or radiation-impermeable contrast media have been proposed. For instance, in the field of angiography using X-rays, the direct-film method, X-ray cinefilm method, and digital subtraction method are known.

The proposed techniques are all relied on a system in which two-dimensional serial photographing from a fixed angle is achieved with injection of an intravascular radiopaque contrast medium. Due to the fixed photographing angle, this system is in many case unable to make a correct diagnosis, e.g. of the extent and site of a coronary stricture (focus responsible for the disease) of the acute myocardial infarction based on a single run of the serial photographing, and subsequently take an appropriate therapeutic treatment, such as PTCA (Percutaneous Transluminal Coronary Angioplasty) without delay. Particularly when the object to be examined is in the dynamic state or in motion, such a fixed-position photographing is almost unable to detect the condition of a portion of the object opposite the view site.

In order to obtain correct information about the object, observation of additional images taken from many different angles is inevitable. Such a multi-angle observation, however, requires repeated photographing entailing synchronous repeated injection of the contrast medium with the resultant prolonged examination time and increased medical radiation exposure.

There have been proposed techniques related to the serial rotation stereography in which a stereoscope is used to observe an image as a stereograph from a desired position. The proposed techniques include special two trains of electronic circuits additionally provided to display analog images or digital subtraction images with predetermined angular phases on two display units, e.g., television monitors (see, Japanese Patent Laid-open Publications Nos. 61-159941 and 2-156778, for example).

The proposed techniques are, however, not available for the simultaneous stereoscopic observation by multiple viewers, nor avails no function thereof against the viewer having an artificial eye. Further, for a viewer who is amblyopic or has visual acuity imbalance, observation itself is complicated and might lead to a severe ocular fatigue.

The photographing technique used in the known serial rotation stereograph apparatus requires 10 sec or more for photographing each unit angle of rotation. In the case where an object to be examined is in motion, such as the left ventricle of an adult heart (though varying with the organs), a 40 cc intravascular contrast medium is forced out from the heart in a short period of time by the blood flow, so that the photographing angle per single injection of the contrast medium is limited to 30° at maximum. In order to photograph the entire 360°, a great amount of intravascular contrast medium must be injected with the result that the object is subjected to undue load. Accordingly, the intended observation of serial or continual photographing conditions is practically impossible.

The prior technique disclosed in Japanese Patent Laid-open Publication No. 61-159941 gives no consideration to the time point when the injected contrast medium images in the object is photographed, and to the manner in which the contrast medium is injected toward a predetermined affected part. Accordingly, there is a risk of the injected contrast medium images at a predetermined portion being photographed inaccurately. In addition, the contrast medium is discharged from the object in a short period of time, as previously described, so the photographing necessarily involves repeated injection of the contrast medium.

In order to avoid halation on a recorded frame image, the use of a filter is inevitable. The fixed filter, when used, must be displaced according to the photographing angle, so that the photographing device has a limitation in its rotation speed.

Stated more specifically, when the photographing apparatus rotates about an object held stationary and having a vertical size (thickness) different from a horizontal size (width), due partly to the difference between the vertical size and the horizontal size of the object, and partly to the rotation of the photographing apparatus, the amount of radiation penetrating through the object is caused to change abruptly at a relatively thin or narrow portion of the object and at an air-containing organ of the object such as lungs, thus causing a halation. In order to prevent the halation, the filter must be displaced in view of the relation between the angular position of the photographing apparatus and the object.

However, since the conventional filters are so constructed as to block unnecessary radiation by means of a clay plate of copper or zinc, they can only deal with an application in which a predetermined field of view is two dimensionally photographed from a predetermined direction with the filter is disposed in a predetermined position (for filtering). When different portions of the same object to be photographed or when the photographing apparatus is rotated, the position of the filter must be changed.

For example, when an abdominal X-ray examination of an object is intended, it is sufficient to previously place a filter well matched in shape and structure with the abdomen of the object. However, when objects to be examined have different abdominal shapes, or when the X-ray examination must be achieved in a fixed time period with respect to both abdomen and chest of the object, the intended X-ray examination cannot be achieved only with the use of a filter disposed to filter the abdominal part. For the chest X-ray examination, the filter must be displaced in position, which displacement is conventionally effected manually with continual observation under the X-ray fluoroscopy.

The manual filtering operation under X-ray fluoroscopic observation is complicated, prolongs the fluoroscoping time and increases the radiation exposure. To overcome these deficiencies, an automatic filtering technique called auto-iris has been proposed.

In the operation of the auto-iris, the distribution of halation varying with the location or site is detected by a sensor to displace the filter to an appropriate filtering position. In despite of the use of the auto-iris, it takes 10 sec or more to turn the photographing apparatus to 180° for photographing an object. Due to this long photographing time, re-injection of the contrast medium is unavoidable, and emission of the pulsed radiation proportional to the photographing time is needed. More particularly, the auto-iris has a critical problem that it cannot deal with high-speed rotation of the photographing apparatus, and the filter has a constant thickness and hence is not adaptable to those objects having different thicknesses or widths.

In the case where a certain portion of a predetermined part of an object is to be continuously photographed by a photographing apparatus fixed at a predetermined angle, an angle to be observed must be found out first to determine the predetermined angle. Thus, the portion to be continuously photographed can not be found out unless multilateral photographing completes in advance.

Furthermore, in the case where the object to be examined is in motion like the heart and entails bleeding from a blood vessel, the conventional photographing time of more than 10 sec for 180° does not ensure observation of actual, continual bleeding condition (functioning condition) of the moving object, but only enables observation of sham dynamic images taken intermittently at regular intervals of time. It is, therefore, extremely difficult to make a precision diagnostic examination of the side and extent of the functioning condition.

Even if the images taken at a low speed are observed in the high-speed serial display mode, observed images are still far different from actual images with the result that observation of the actual continual dynamic condition (live images) on the real-time basis is still unachievable.

The rotation speed and the photographing time of the radiographic apparatus are important factors to improve the clinical usefulness. This is because in the angiocardiography, aortography, cavography, pulmonary angiography, coronary arteriography, and angiography for other great vessels, a correct diagnosis can be pronounced by virtue of three-dimensional or stereoscopic understanding of the form and structure of blood vessels and observation of the function and blood flow condition.

To this end, in the case of the heart, for example, observation should preferably be achieved at high speeds under the condition that a single stroke of diastolic and systolic phases (one heartbeat) of the heart is observed in a predetermined angle ranging from 10° to 90°, and preferably from 30° to 50°, the predetermined heart rate is at least 2 to 6, and preferably about 4; and the rotation angle is 360° or several times greater than 180°.

In the prior art, no consideration is given to the one-heartbeat observation angle, the rotation angle, and rotation photographing time synchronized with the heart rate of an object to be examined. Particularly, in the angiography of an object consisting of heart and great vessels or a solid organ, no account is taken on the peculiarity of photographing conditions. Namely, in the case of the angiocardiography or the solid organ angiography, the peculiarity of the object is left out of consideration.

The prior art is generally limited to a continuous photographing over an angle of 180° extending from the left side to the right side, and when it is used in the angiography, angiographic images in the range of 180° can be obtained. However, when the angiography is started from an arbitrary angle $\alpha°$, it is only possible to obtain images in an angular range of 180°-$\alpha°$ because the maximum photographing angular range is 180°, as described above.

This is partly because the photographing apparatus according to prior art do not rely on the standpoint of photographing live images at high speeds as in the present invention, but aim at a solution of the problems associated with low-speed photography over an angle of 180°, and partly because the prior filters are only adaptable to the photographing range of 180°.

In the case where an object to be examined is cardiac great vessels, and particularly when an intravascular contrast medium is injected into the right atrium for image formation, the prior art having a photographing angular range of 180° cannot perform the serial rotation imaging of a system composed in sequence of vena cavae-right atrium-right ventricle-pulmonary artery-pulmonary veins-left ventricle-left atrium-aorta-peripheral vessels-vena cavae, along the direction of flow of the contrast medium. This is also true in the angiography of solid organs represented by carcinomas.

In the prior technique using digital subtraction (Japanese Patent Laid-open Publication No. 2-156778, for example), mask images are photographed and these mask images and contrast medium images are subtracted. However, since the contrast medium images are sham dynamic images taken intermittently at regular intervals of time, this prior technique has a critical drawback that even if the images taken at a low speed are merely observed in the high speed continuous display mode, the observed images are still far different from actual images.

The prior art still has problems left unsettled: the disadvantage inflicted on an object or patient due to the medical radiation exposure, and the dose-dependent side effect of the radiopaque contrast medium. That is, a radiographic observation accompanying a great dose of radiopaque contrast medium necessarily involves a medical radiation exposure injury concentrated particularly at the gonad, bone marrow and thyroid gland.

The present inventors conceived the present invention through diligent researches in the subjects of: a filter adaptable for the serial high-speed rotatography; stereoscopic or three-dimensional understanding of the form and structure of an object and serial photography of the actual dynamic condition; serial or continuous photographing of the function and blood flow condition of the object (live-image photographing); photographing the object in a short period of time from every possible angle without forming a dead angle with a single injection of usual dose of a radiopaque contrast medium for reducing the radiation exposure and the dose of the radiopaque contrast medium; photographing from an arbitrary angle over an optimal angular range; photographing over the entire 360° starting from any angular position; and three-dimensional understanding of the object and precision diagnostic examination of the object made correctly on the real-time basis in terms of the distance, area and volume.

It is accordingly an object of the present invention to provide a K-filter which is suitable for the serial high-speed rotatography and capable of achieving a desired filtering operation even when a photographing apparatus turns 180° or more or 360° from an arbitrary position.

Another object of the present invention is to provide an apparatus for the serial high-speed rotatography, which is capable of continuously photographing the actual dynamic state of an object in a short period of time by carrying out the serial high-speed rotatography.

A further object of the present invention is to provide a serial high-speed rotatograph apparatus which is capable of photographing an object in a short time from an arbitrary angle without forming a dead angle and accompanying only a single dose or injection of a radiopaque contrast medium, thus reducing the radiation exposure and the amount of radiopaque contrast medium used.

Still another object of the present invention is to provide an serial high-speed rotatograph apparatus which is capable of determining an optimal photographing time for the rotatography of each of different objects susceptible to influences from the heart rate, which is capable of photographing an image to enable stereoscopic understanding of the form and structure of the object, and which is able to continuously photographing the function and blood flow condition of the object.

Yet another object of the present invention is to provide a serial high-speed rotatograph apparatus which is capable of achieving photographing from an arbitrary angle within an optimal angular range in accordance with the heart rate.

DISCLOSURE OF THE INVENTION

A K-filter of the present invention for serial high-speed rotatography is one attached to an apparatus for the serial high-speed rotatography for photographing an object to be examined by use of X-rays. The K-filter comprises two K-containers each defining a space fluidly containing therein a radiopaque fluid substance, and a radiotransparent region formed between the two K-containers. The K-containers are pivotally supported by a supporting member and are of the inversion type which allows the radiotransparent-region sides of the K-containers to move.

More specifically, the supporting member is formed with a bearing portion, and the K-containers each have a pivot shaft rotatably supported by the bearing portion. As the radiopaque fluid substance in each of the K-containers moves by gravity, the K-container turns about the pivot shaft to angularly move its radiotransparent-region side. Preferably, the K-containers each have opposite sides having the shape of an isosceles triangle. The inside surface of at least the radiotransparent-region side of each of the K-containers is preferably covered with a coating material.

Preferably, the pivot shaft is adjusted in position by a position control motor in synchronism with rotation of the serial high-speed rotatograph apparatus. It is preferable that at least one of the K-containers is moved to render respective movements of the two K-containers asymmetric with each other.

The radiopaque fluid substance is preferably filled in the K-containers to the extent of 10% to 50% of the capacity of the K-containers. It is preferable that the bearing portion is displaceable relative to the supporting member, or the K-containers are detachably mounted on the supporting member.

The radiotransparent region of the inversion type K-filter preferably has a substantially elliptical shape or a substantially circular shape.

An apparatus of the invention for serial high-speed rotatography is disposed concentric with an object to be examined and rotatable for photographing the object. The serial high-speed rotatograph apparatus comprises a radiation tube device having attached thereto the K-filter described above.

The radiation tube device constituting the apparatus is preferably so constructed as to emit pulsed exposure of radiation selectively at predetermined intervals of an unit angle and at predetermined intervals of time. Preferably, the serial high-speed rotatograph apparatus is rotatable to 180° in 5 seconds or less, or to 360° in 10 seconds or less, and the serial high-speed rotatograph apparatus while at rest is capable of emitting pulsed exposure of radiation for 2 to 4 seconds at intervals of time which correspond to the predetermined intervals of the unit angle.

It is preferably that the rotation photographing time of the serial high-speed rotatograph apparatus is determined by an angle for observing one heartbeat of the object, a rotation angle, and a heart rate of the object. More specifically, a predetermined range of one-heartbeat observation angle ($\delta°$), a predetermined rotation angle ($SR°$), and a predetermined heart rate from a synchronous electrocardiograph are inputted in an arithmetic unit to set a rotating speed corresponding to the rotation photographing time, and a signal representing the rotating speed is sent to a rotation controller for controlling the serial high-speed rotatograph apparatus, the rotation controller controlling the rotation photographing time. The rotation photographing time ($\theta$ sec) of the serial high-speed rotatograph apparatus is obtained and given by: $\theta (sec) = SR° \times t / (\eta \times \delta°)$, where $SR°$ is the rotation angle, t is the unit time, $\eta°$ is the number of heartbeats per unit time t, and $\delta°$ is the one-heartbeat observation angle. When the unit time t is one minute, then the above-mentioned equation can be written as:

$$\theta(sec) = SR° \times 60 / (\eta \times \delta°).$$

The serial high-speed rotatograph apparatus is preferably rotatable to at least 360° and more desirably is capable of conducting reciprocating photographing while it is rotating alternately in the forward and reverse directions. The reciprocating photographing may be achieved by rotating the apparatus to 180° or 360° alternately in the forward and reverse directions, thus making it possible to perform continuous photographing. When the rotating angle is 180°, the serial high-speed rotatograph apparatus preferably further has a rotatable region extending contiguously from each end of the 180° over an angle of 30°.

When the serial high-speed rotatograph apparatus is rotating at high speeds, the radiopaque fluid substance in the inversion type K-filter flows inside the K-containers to follow up the posture of the apparatus to conduct filtering appropriate to the condition of the object, thereby precluding the occurrence of halation.

In sum, the K-filter comprises two K-containers each defining a space fluidly containing therein a radiopaque fluid substance, and a radiotransparent region formed between the two K-containers. The K-containers are not fixed to, but pivotally supported by, a supporting member so that the radiotransparent-region sides of the K-containers are movable along angular paths. Thus, when the serial high-speed rotatograph apparatus is rotated at a high speed to more than 180°, the K-containers turn or pivot relative to the supporting member to conduct filtering under any conditions such as an inclined posture, not the horizontal posture, under which photographing is started. When the serial high-speed rotatograph apparatus is in a lower inclined position located below the horizontal position, the K-containers turn about the pivot shafts to keep their radiopaque-fluid-substance-containing spaces in respective inclined positions appropriate to conduct filtering. The radiopaque fluid substance flows to conform to the inclined postures of the respective the K-containers, so that appropriate filtering can be achieved without causing halation.

The inversion type K-filter is attached to a radiation tube device constituting the serial high-speed rotatograph apparatus. When the serial high-speed rotatograph apparatus is rotated at high speeds while projecting radiation pulses to conduct continuous photographing, the inversion K-filter compensates for an area on an image saturated with radiation (i.e., halation) at any angular position or at any point of time during rotation over 360°. Consequently, high quality images can be formed.

At any angular position on 360°, the inversion type K-filter properly restricts the radiation so that scattering of the radiation (X-rays) inside the object is reduced to lesser the effect of the secondary radiation (X-rays) on the images, thereby preventing degradation of the images and reducing the medical radiation exposure.

In this instance, if the radiotransparent region has a substantially elliptical shape, owing to this shape the radiotransparent region is particularly suitable for use in the angiocardiography and thoracic angiography. Further, a K-filter having a substantially circular radiotransparent region is suitable for use in the cerebral angiography.

The radiation tube device which constitutes the serial high-speed rotatograph apparatus can emit pulsed radiation selectively at predetermined intervals of the unit angle and at predetermined intervals of time, so that by a single photographing step, continuously rotating images and serial images at a predetermined position can be obtained with respect to the same object. Thus, the serial images at the predetermined position and the continuously rotating images can be observed in the same and series state.

Since the rotation photographing time of the serial high-speed rotatograph apparatus is determined by the angle for observing one heartbeat, the rotation angle, and the heart rate of the object, photographing can be carried out at a rotation photographing time appropriate to the heart rate which varies with the individual object. In order words, the rotation photographing time can automatically be determined by setting a predetermined range of one-heartbeat observation angle ($\delta°$) and a predetermined rotation angle (SR°).

Thus, in agreement with changes or fluctuations of the heartbeats of the object, it is possible not only to take images which enable stereoscopic understanding of the form and structure of the object, but also to continuously photograph the function and blood flow condition of the object as live images. A fine diagnostic examination can, therefore, be achieved.

The rotation photographing time ($\theta$ sec) of the serial high-speed rotatograph apparatus may be obtained and given by: $\theta$ (sec)=SR°×t / ($\eta$×$\delta°$), where SR° is the rotation angle, t is the unit time, $\eta$ is the number of heartbeats per unit time t, and $\delta°$ is the one-heartbeat observation angle, or alternatively by $\theta$ (sec) =SR°×60 / ($\eta$×$\delta°$) when the unit time t is one minute. Thus, for each of different objects which differ from one another depending on the heart rate, an optimal rotation photographing time can be obtained with the result that photographing is achieved in interlocking relation to changes or fluctuations of the heartbeats.

Regarding the object susceptible to influences from the blood flow, images which enable understanding of the form and structure of the object can be taken by photograph. In addition, it is possible to continuously photograph the function and blood flow of the object which is susceptible to influences from the heartbeat. Photographing the function and blood flow of the object is highly contributive to the pronouncement of a correct diagnosis.

Furthermore, the photographing time may be cut down to reduce the radiation exposure and the dose of radiopaque contrast medium, and with only a single injection of the radiopaque contrast medium the object may be photographed from a desired arbitrary angle.

Since the rotation angle of the serial high-speed rotatograph apparatus is at least 360°, photographing can be conducted from an arbitrary angle, over an angular range and a rotation photographing time that are optimal to the heartbeat. The serial high-speed rotatograph apparatus may be so constructed as to conduct swing or oscillatory photographing, or to conduct continuous photographing while it is rotated alternately in the forward and reverse directions over an angle of 180° or 360°. Thus, a predetermined portion can be observed as a real image in a predetermined period of time and in a predetermined range. This is extremely useful in practical application.

With the use of the serial high-speed rotatograph apparatus described above, variable conditions of the object in a short period of time can be photographed and observed as live images. For example, in the case where the object is an organ which is in motion, such as the heart, and hence susceptible to influences from the heartbeat, when the number of heartbeats per minute ($\eta$) is 120, and if an observation is executed under the condition that the one-heartbeat observation angle ($\delta°$) is 30°, and the rotation angle (SR°) is 360°, then the rotation photographing time ($\theta$ sec) of 6 can be obtained by performing $\theta$ (sec)=SR°×60 / ($\eta$×$\delta°$).

This means that rotation photographing achieved over an angle of 360° in 6 seconds can provide excellent images which are useful for diagnostic examination. If an angle of 180° is to be observed, the photographing will be performed in 3 second. Thus, when a viewer or observer determines values for the range of $\delta°$ and the SR°, respectively, in view of the condition of disease and the kind of organ to be examined, the number of heartbeats per minute is automatically inputted into the arithmetic unit to set a rotating speed corresponding to a calculated rotation photographing time. A signal representing the rotation speed is sent to the rotation controller which controls the rotation photographing time for controlling the serial high-speed rotatograph apparatus.

Particularly, when an observation is intended under the condition that the number of heartbeats per minute is 120, $\delta°$ is 30° and the rotation angle is 360°, and if imaging is executed for 6 second which is the rotation photographing time calculated by the aforesaid equation, and with injection of a 40 cc intravascular contrast medium into the right atrium in a system (cardiac great vessel system) composed in sequence of: vena cavae-right atrium-right ventricle-pulmonary artery-pulmonary veins-left atrium-left ventricle-aorta-peripheral vessels-vena cavae, the imaging will start from the right atrium and continue for 6 seconds during which time a part of the system including: right ventricle-pulmonary artery-pulmonary veins-left atrium-right ventricle can be imaged. In this instance, that portion of the system extending between the right atrium and the right ventricle is imaged first with excellent qualities which are useful for diagnostic examination. As the contrast medium flows downstream, that portion of the system extending between the left atrium and the left ventricle can be imaged. Thus, excellent images useful for diagnostic examination can be obtained over the entire 360°.

Similarly, in the angiography for a parenchymal or solid organ, such as a carcinoma, a system composed in sequence of: arterial phase-parenchymal phase (contraststaining of carcinoma)-venous phase can be imaged in the same manner as described above.

These images thus taken can be displayed with improved clearness on a single monitor as live images which represent the actual dynamic or moving state of the object without change.

Since the apparatus is rotatable concentrically about the object to conduct the rotation photographing, all the images are projected from different angles but are equidistant from the apparatus.

The serial high-speed rotatography makes it possible to continuously photographing the actual dynamic or moving state in a short time of the object as it is.

As described above, according to the present invention, the photographing time can be cut down, and the radiation dose and the amount of a radiopaque contrast medium can be reduced, however, only with a single injection of the radiopaque contrast medium, the object to be examined can be photographed from every possible angle without forming a dead angle. Furthermore, for each individual object susceptible to influences from the heart rate, an optimal rotation photographing time can be determined. It is therefore possible to form images which enable stereoscopic or three-dimensional understanding of the form and structure of the object and to continuously photograph the function and blood flow of the object. Thus, a fine diagnostic examination can, therefore, be achieved.

By virtue of a short photographing time, an additional photographing from a different angle is no longer needed with the result the dose or injection of the radiopaque contrast medium as well as the radiation dose can be reduced, thus lessening the medical radiation exposure to a greater extent.

Various other advantages of the present invention will become apparent from the following description.

BEST MODE FOR CARRYING OUT THE INVENTION

Figure 1:
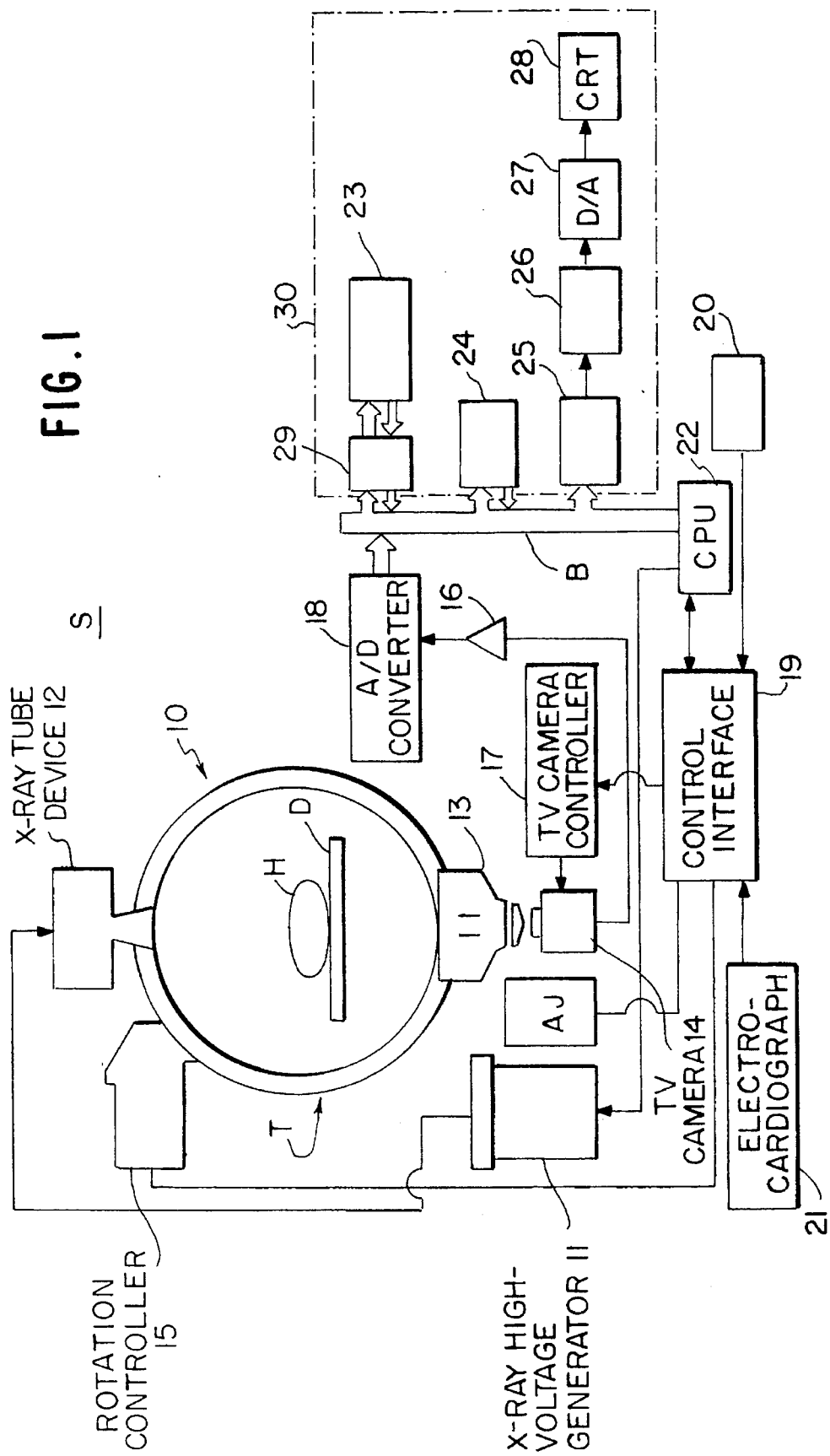
FIG. 1 is a block diagram of an apparatus related to the present invention.

One embodiment of the present invention will be described hereinbelow in greater detail with reference to the accompanying sheets of drawings. It is to be understood that components and arrangements described below are illustrative and not restrictive, and various minor changes and modifications are possible without departing from the scope of the gist of the present invention. In the embodiment described below, radiation is in the form of X-rays but should by no means be limited to this form of radiation.

Description will be first given of the construction of an apparatus 10 for serial high-speed rotatography. In the illustrated embodiment, the serial high-speed rotatograph apparatus 10 employs X-rays as radiation and includes a circular cylinder (rotary stage) T disposed concentrically with the longitudinal axis of an object H placed on an examination table D. The cylinder (rotary stage) T has formed in its inner peripheral surface a photographing slit (not shown).

Formed at an outer peripheral position of the photographing slit is a high-speed rotation device (not shown) which ensures rotation over an angle more than 360°. The high-speed rotation device is provided with a known technique such as a high-speed rotation motor, and a rotation control device or controller 15 for controlling rotation of the motor. The rotation controller 15 is connected via a control interface 19 to a central processing device (CPU) 22.

The serial high-speed rotatograph apparatus 10 further includes an automatic X-ray contrast medium injection device AJ, an X-ray high-voltage generating device or generator 11, an X-ray tube device 12, an image intensifier 13, and an image pick-up device composed of an X-ray television camera 14.

The high-speed rotation device (not shown), the rotation controller 15, the X-ray tube device 12, the image intensifier 13 and the X-ray television camera 14 that constitute the serial high-speed rotatograph apparatus 10 are capable of photographing the object H concentrically about the axis of the object H and at angular intervals of each unit angle. These structural components may be composed of known devices, respectively.

The X-ray high-voltage generator 11 is connected to the CPU 22 by a signal line. The rotation controller 15, an X-ray television camera controller 17, a keyboard 20 as an external input means, and a synchronous electrocardiograph 21 are connected by signal lines to the control interface 19 which in turn is connected via a signal line to the CPU 22.

The serial high-speed rotatograph apparatus 10 is controlled by a command supplied from the CPU 22 based on information including the one-heartbeat observation angle (δ°) and the rotation angle (SR°) that are inputted from the keyboard 20 as well as heartbeat information inputted from the synchronous electrocardiograph 21.

The X-ray television camera 14 has an output terminal connected to an input terminal of a logarithmic amplifier 16 whose output terminal is connected to an input terminal of an analog-to-digital (A/D) converter 18 which converts electric signals representing images acquired upon injection of an X-ray contrast medium, from an analog representation into a digital representation. The A/D converter 18 is connected to a bus B which in turn is connected to the CPU 22.

The automatic X-ray contrast medium injector AJ is connected via a signal line to the control interface 19 so that it is operable in synchronism with the operation of the X-ray high-voltage generator 11, the X-ray television camera controller 17 and the rotation controller 15 according to a command supplied from the CPU 22, In the illustrated embodiment there is provided a digital image processing unit which is composed of the aforesaid A/D converter 18, a file memory 23 serving as a storage device for storing a digital image signal per each unit angle obtained by the A/D converter 18, a frame memory 24, a display memory 25, an enhancer 26 serving as a window processor for windowing the digital image, a digital-to-analog (D/A) converter 27 for converting the digital signal from the enhancer 26 into a digital representation, an X-ray television monitor 28 serving as a display device, and an interface 29 between the file memory 23 and the bus B.

In the serial high-speed rotatograph apparatus 10, angular scanning of the object H starts from a given angular position (i.e., arbitrary angle) and advances over a predetermined angular range about the axis of the object H with an angular increment of the unit angle. An image scanned at each unit angle is converted into digital pulses by a single A/D converter 18 by reading electric image signals through the progressive readout method.

The digitized images are recorded in a single high-speed dynamic RAM (D-RAM) 30 and displayed in sequence on a single X-ray television monitor 28 as serial two-dimensional (2-D) planar images scanned at respective unit angles.

These parts of the D-RAM 30 which function as the file memory 23, the frame memory 24 and the display memory 25 are disposed in parallel on a single bus B which is connected to the CPU 22 as described above. The entire system described above is controlled by the CPU 22 according to commands supplied from the keyboard 20 or the like external input device.

In the illustrated embodiment, the X-ray tube device 12 has attached thereto an inversion type K-filter 1 for the serial high-speed rotatography, such as shown in FIGS. 2 through 5. The inversion type K-filter 1 comprises a supporting member 1a having the shape of a rectangular parallelopiped, and two K-containers 5a, 5b having opposite side surfaces 5c having the shape of an isosceles triangle.

The K-containers 5a, 5b and the supporting member 1a are formed from an radiotransparent material which allows the passage of X-rays. The K-containers 5a, 5b are preferably made from a synthetic resin (e.g., thermoplastics print) which can readily be thermally processed.

The K-containers 5a, 5b each have an internal space 3a, 3b fluidly containing therein a radiopaque fluid substance 4 which is opaque or impermeable to X-ray (in this context also referred to as "X-ray contrast medium"). The opposite side surfaces 5c of each of the K-containers 5a, 5b have an isosceles triangular shape, and the two K-containers 5a, 5b are pivotally supported by the supporting member 1a, with their apexes 5d confronted with each other. Between the two K-containers 5a, 5b is formed a radiotransparent region (X-ray permeable region) 2 of a predetermined shape and configuration.

Figure 2:
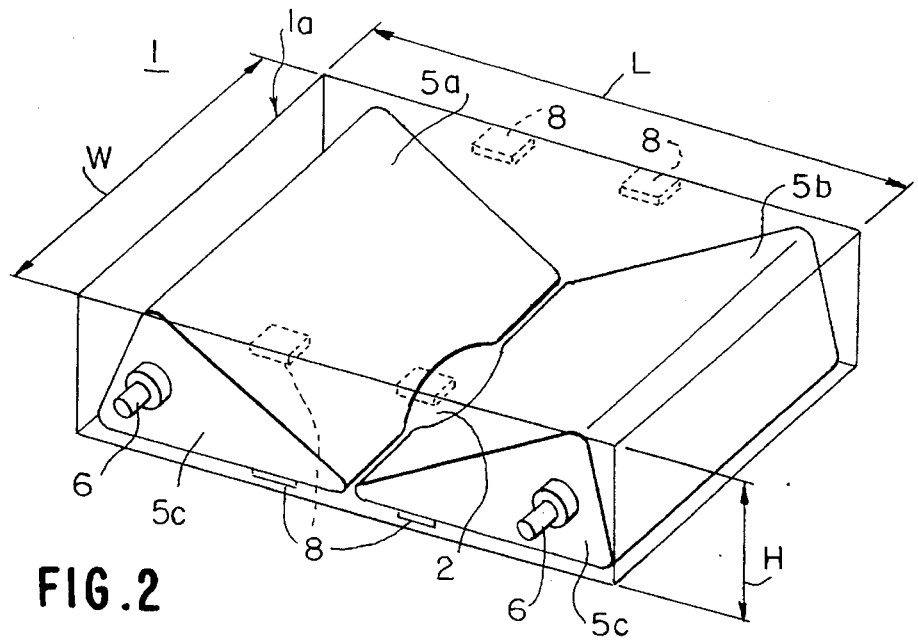
FIG. 2 is a perspective view of an inversion type K-filter according to one embodiment of the present invention.

Thus, the inversion type K-filter 1 in this embodiment includes a supporting member 1a and two K-containers 5a, 5b that are formed from an X-ray permeable material. As shown in FIG. 2, the supporting member 1a has a predetermined length L, a predetermined width W and a predetermined height H. It has a pair of aligned bearing portions formed in opposite side walls adjacent to each of opposite ends of the supporting member 1a. The K-containers 5a, 5b are received in the supporting member 1a and each journaled on the corresponding pair of bearing portions of the supporting member 1a.

Figure 3:
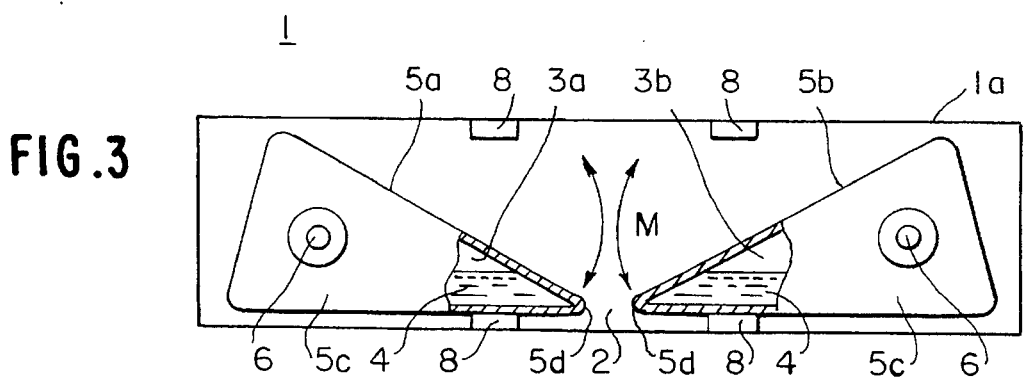
FIG. 3 is a side view of FIG. 2.
Figure 4:
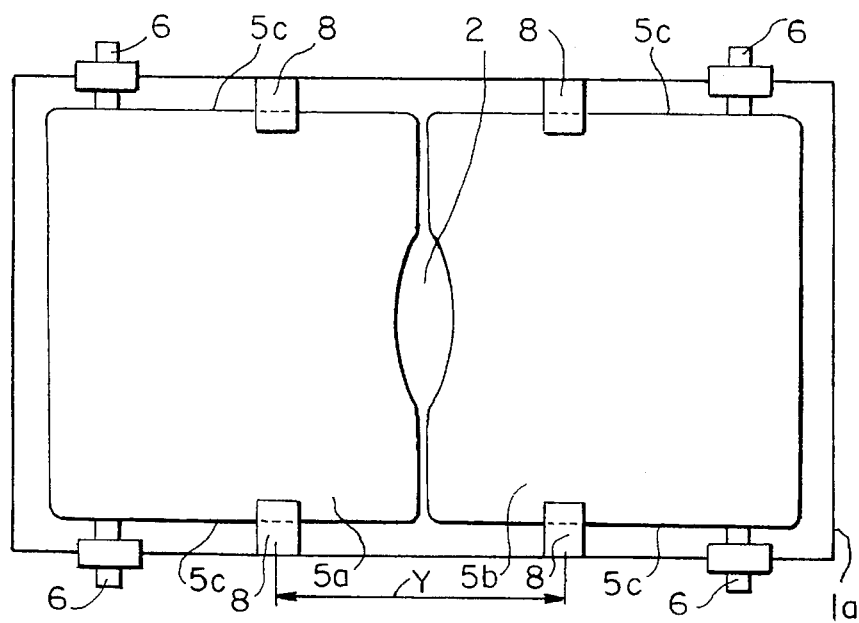
FIG. 4 is a plan view of the inversion type K-filter shown in FIG. 2.
Figure 5:
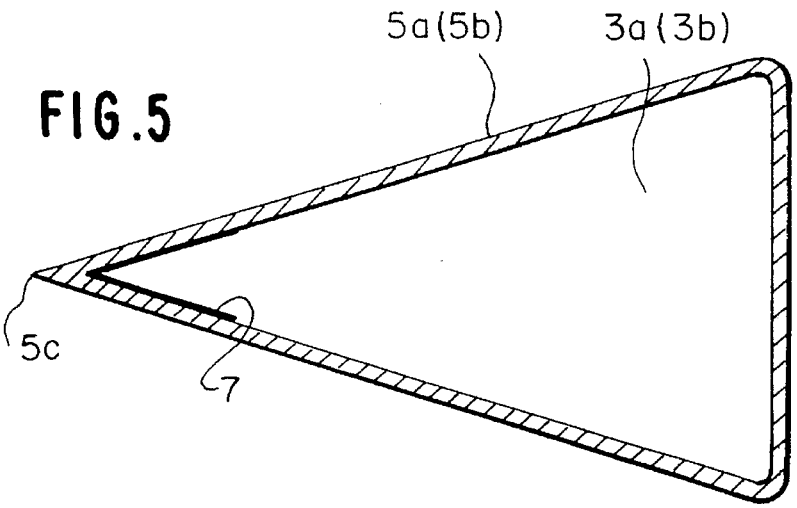
FIG. 5 is an enlarged schematic cross-sectional view of a K-container.

A pair of aligned support shafts 6, 6 projects outwardly from the opposite side surfaces 5c of each of the K-container 5a, 5b at respective portions remote from the X-ray permeable region 2. The supporting shafts 6, 6 are rotatably received in the corresponding bearing portions of the supporting member 1a. As shown in FIG. 3, the K-containers 5a, 5b are pivotally movable about the support shafts 6 in the direction of the arrow M by the action of the weight of the respective K-containers 5a, 5b or the weight of the radiopaque fluid substance 4 contained therein. In the illustrated embodiment, the radiopaque impermeable fluid substance 4 is filled in the K-containers 5a, 5b to such an extent of from 10% to 50% of the capacity of the K-containers 5a, 5b.

The radiopaque or X-ray impermeable fluid substance 4 may include a contract material, a solution of iodine (I), a solution of bromine (Br), and an water-soluble agent of any other X-ray impermeable atom. The X-ray impermeable fluid substances 4, though it may vary depending on the type of the object to be examined, is preferably composed of a 120 mgI/ml–40 mgI/ml iodic solution, such as known under designations "Optiray" (Yamanouchi Pharmaceutical Co., Ltd.), "Gastrogrfin" (Nippon Schering) and the like. The X-ray impermeable fluid substance 4 should by no means be limited to liquid but may be powder or fine particle as long as the desired flowability is maintained.

A region or portion of the internal space defined in each of the K-containers 5a, 5b adjacent to the X-ray permeable region 2 has a rounded profile which is free from a sharp edge and hence is able to guarantee a desired flowability of the X-ray impermeable fluid substance 4. Thus, when the K-containers 5a, 5b turn about the supporting shafts 6, the X-ray impermeable fluid substance 4 is able to flow smoothly away from the X-ray permeable region 2 without staying at the X-ray permeable-region 2 sides of the respective K-containers 5a, 5b. Thus, the X-ray impermeable fluid substance 4 is prevented from being accidentally projected by the X-ray which would otherwise result in degradation of the image qualities.

Figure 6:
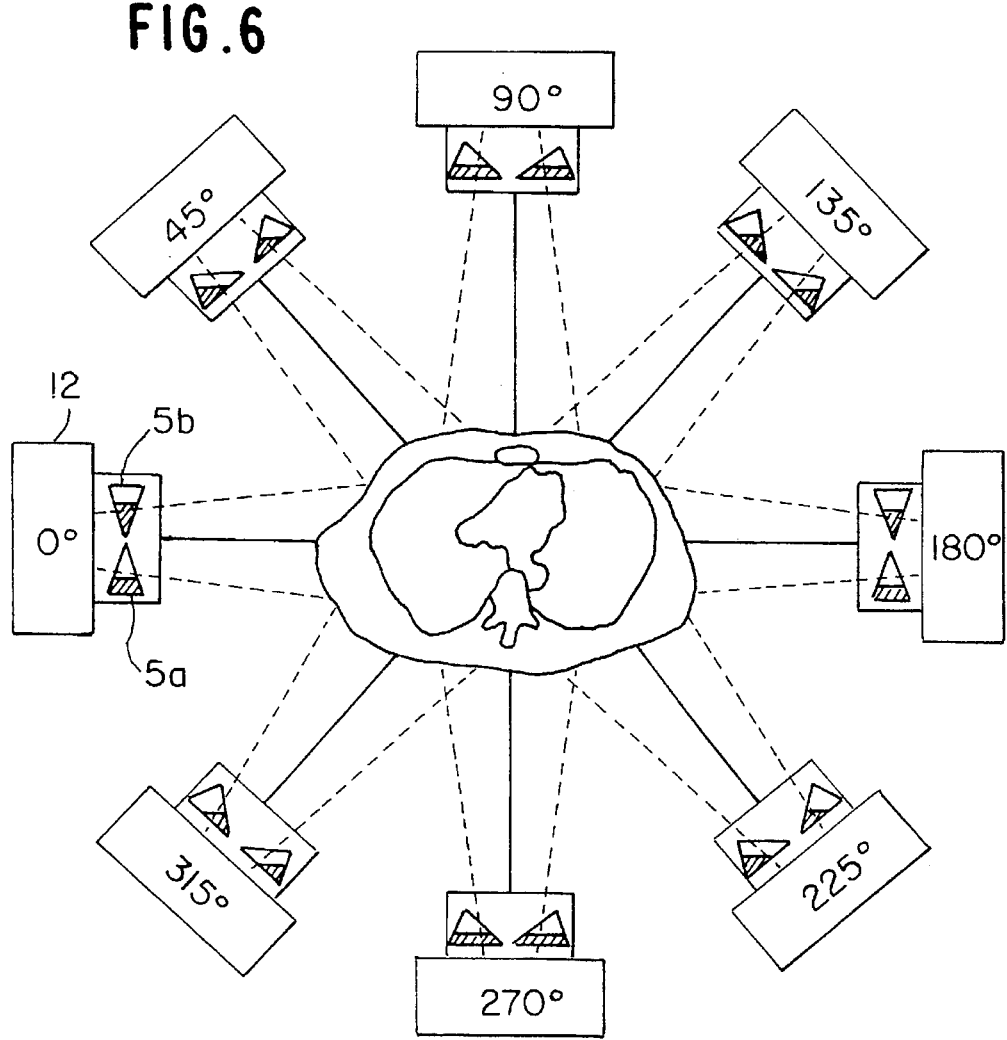
FIG. 6 is a diagrammatic view illustrative of the operation of the inversion type K-filter of FIG. 2.

In place of the rounded profile in the above-mentioned embodiment, the inside surface of each of the K-containers 5a, 5b may be covered with a coating material 7 at least over a region adjacent to the radiotransparent region 2, as shown in FIG. 6. The coating material 7 used in the illustrated embodiment is composed of silicone grease. With this coating 7, the X-ray impermeable fluid substance 4 can flow smoothly even when respective corners on the radiotransparent region 2 side of the K-containers 5a, 5b have an acute angle. Thus, even when the X-ray tube device 12 is angularly moved or turned from the 90° position to the 135° position shown in FIG. 6, the X-ray impermeable fluid substance 4 contained particularly in the K-container 5b on the lower side is able to flow rapidly into an appropriate position without staying or standing at the radiotransparent-region 2 side corner edge of the same lower K-container 5b. This is extremely useful in practical application. The coating material 7 should by no means be limited to the silicone grease but may include a fluoroplastic coating and any other material which is able to guarantee the flowability of the X-ray impermeable fluid substance 4.

The K-containers 5a, 5b may preferably be evacuated to improve the flowability of the X-ray impermeable fluid substance 4 contained in the thus evacuated or vacuum K-containers 5a, 5b. The above-described K-filter 1 may preferably be variable in shape and dimensions depending on the type, shape and configuration of the object H to be examined. For instance, a K-filter 1 adapted to be used with a smaller object H having a smaller width has a height H which is larger than the height of a different K-filter adapted to be used with a larger object H having a larger width.

The range of angular movement of the K-containers 5a, 5b is determined by the construction of the supporting member 1a by means of which the K-containers 5a, 5b are pivotally supported. The supporting member 1a in turn is in dependence upon the size of the X-ray tube device and a multiple diaphragm, In general, the extent of angular movement of the K-containers 5a, 5b may be in the range of about 20% of the respective sizes of the x-ray tube and the multiple diaphragm. For example, the X-ray permeable-region 2 sides of the K-containers 5a, 5b are preferably movable about the support shafts 6 over a distance of 2 cm to 10 cm.

As shown in FIGS. 2 and 3, a plurality of cushioning members 8 made, for example, of sponge are attached to appropriate portions (two on each of the upper and lower interior surfaces in the illustrated embodiment) of the supporting member 1a for absorbing a shock force to prevent generation of unpleasant noise when the K-containers 5a, 5b abut against the supporting member 1a.

In order to attach the inversion type K-filter 1 of the foregoing construction to the X-ray tube device 12, locking hooks (not shown) are previously attached to the front surface of the X-ray tube device 12 for a purpose of hooking or interlocking the K-filter 1 and the supporting member 1a. The locking hooks may have an appropriate shape complementary in contour to the shape of the supporting member 1a. As an alternative, the supporting member 1a may be provided with permanent magnets which enable the supporting member 1a to be attached to the X-ray tube device 12 by attracting magnetic forces of the permanent magnets.

Instead of using a detachable supporting member 1, the inversion type K-filter 1 may be used in combination with a master cassette so that various inversion type K-filters of different sizes can be selectively and detachably mounted in the master cassette to conform to various types of objects to be examined. Further, the X-ray tube device 12 may be provided with a bracket for supporting thereon the K-filter 1, which bracket is movably constructed such that the position of the K-filter can easily be adjusted by a remote control.

When the object H to be examined is an organ of the human body, the X-ray permeable region 2 of the K-filter 1 is preferably shaped into an appropriate form which is suited for the anatomical shape of the organ. The X-ray impermeable fluid substance 4 is flowable under the action of the gravitational force, centrifugal force and the like in response to the high-speed rotational movement of the X-ray tube device 12.

With this movement of the X-ray impermeable fluid substance 4, the width Y (FIG. 4) of a portion or region in the vicinity of the X-ray permeable region 2 and excluding the X-ray permeable region 2 are variable so that the area of an unfiltered region is increased and decreased arbitrarily.

FIGS. 8 through 11 show several different inversion type K-filters according to further embodiments, wherein these components which are like or corresponding to those of FIGS. 2–5 are designated by the corresponding reference characters, and further description thereof will be omitted.

Figure 8:
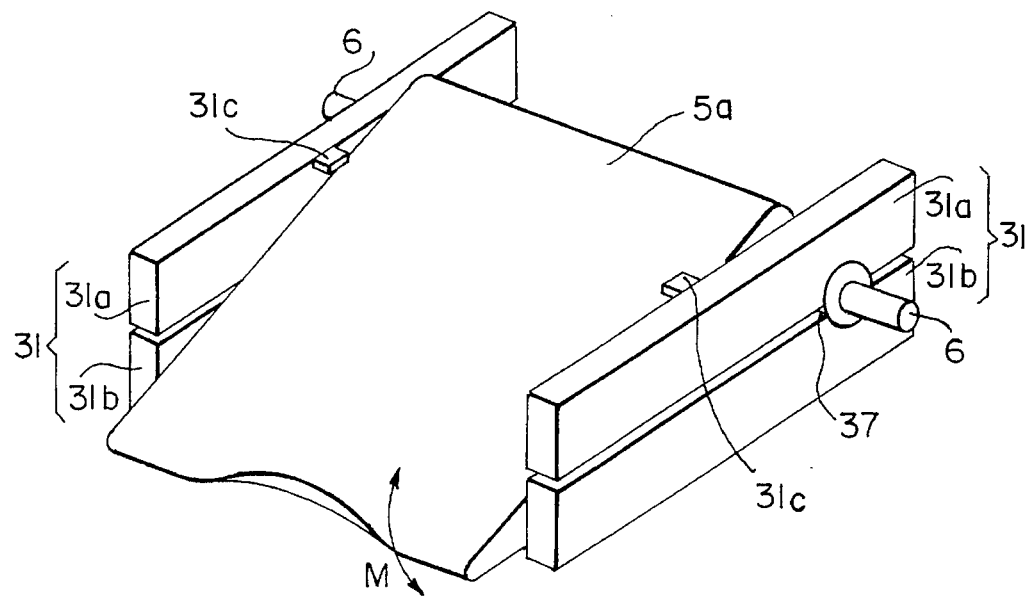
FIG. 8 is a perspective view showing a portion of an inversion type K-filter according to another embodiment of the present invention.

In the embodiment shown in FIG. 8, only one K-container 5a is illustrated. As against the box-like supporting member 1a of the inversion K-filter 1 shown in FIGS. 2–5, the supporting member 1a shown in this embodiment includes a pair of laterally spaced support members 31, 31 each composed of a pair of parallel vertically spaced upper and lower elongated plate members 31a and 31b. The K-container 5a, (5b) is structurally the same as one shown in the first embodiment described above. Each pair of upper and lower plate members 31a, 31b has a bearing portion formed jointly by two confronting, substantially semicircular recessed portions 37 located adjacent to one end of the plate members 31a, 31b.

The upper and lower plate members 31a, 32b are formed with a pair of vertically aligned stoppers 31c (one stopper on the upper plate member 31a being shown) projecting inwardly from upper and lower edges of the plate members 31a, 31b, respectively, for limiting the movement of the K-container 5a in the direction indicated by the arrow M. The upper and lower plate members 31a, 31b on each side the supporting member 1a are firmly connected together by means of a connector (not shown). With this arrangement, the same operation and effects as those of the first embodiment can be attained. Furthermore, since the upper and lower sides of the supporting members 31, 31 are open, the K-container 5a may be enlarged at its bottom side (that is, as shown in FIG. 8, the bottom side of each of the triangular side surfaces of the K-container 5a may projects vertically outwardly from the upper and lower surfaces of the plate member 31a, 31b), thus providing an enlarged range of angular movement of the K-container 5a.

Figure 9:
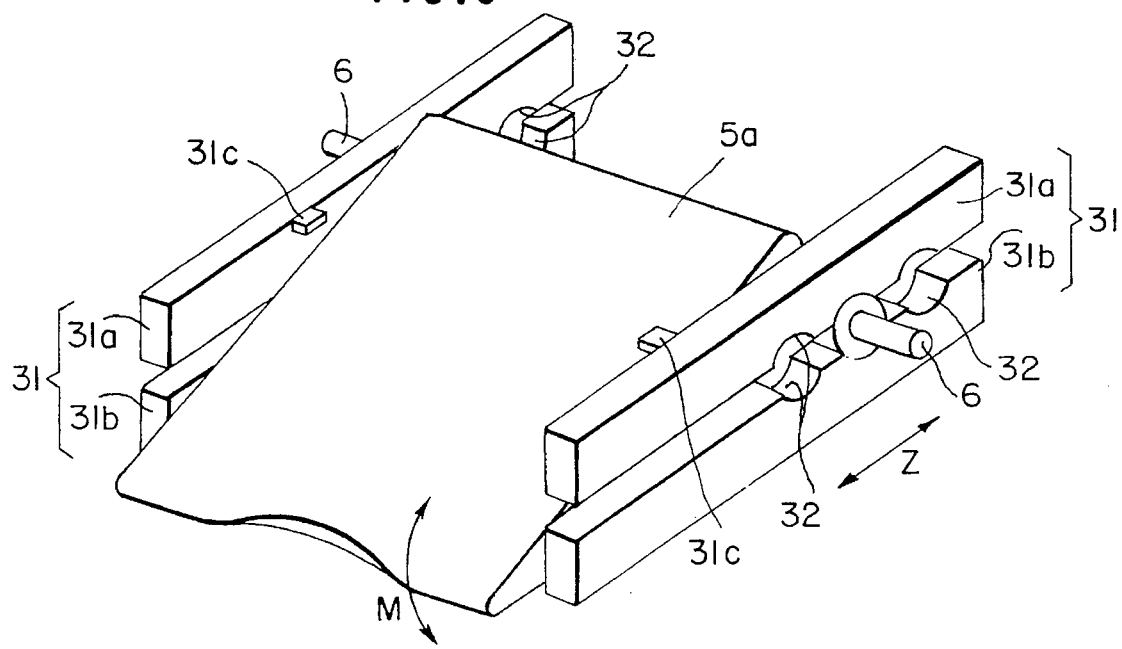
FIG. 9 is a view similar to FIG. 8, showing an inversion type K-filter according to still another embodiment of the present invention.

In the embodiment shown in FIG. 9, the supporting member 1a includes a pair of parallel vertically spaced upper and lower plate members 31a, 31b on each of the left and right sides of the supporting member 1a, in the same manner as shown in FIG. 8. The upper and lower plate members 31a, 31b are connected together at predetermined positions (not designated). Opposed inner surfaces of the upper and lower plate members 31a, 31b are cutout to provide a plurality of recesses 32 (three in the illustrated embodiment) arranged longitudinally of the plate members 31a, 31b for receiving therein a corresponding support shaft 6 of the K-container 5a to enable the K-container 5a to pivotally move about the support shafts 6.

Accordingly, by selectively setting the support shaft 6 in a desired one of the plural recesses or bearing portions 32, it is possible to displace the K-container 5a in the direction of the arrow Z. With this arrangement, the extent of the X-ray permeable region 2 which is defined between the two K-containers 5a, 5b (only one container 5a being shown) can be adjusted in view of the size and the like factor of the object H to be examined.

Figure 10:
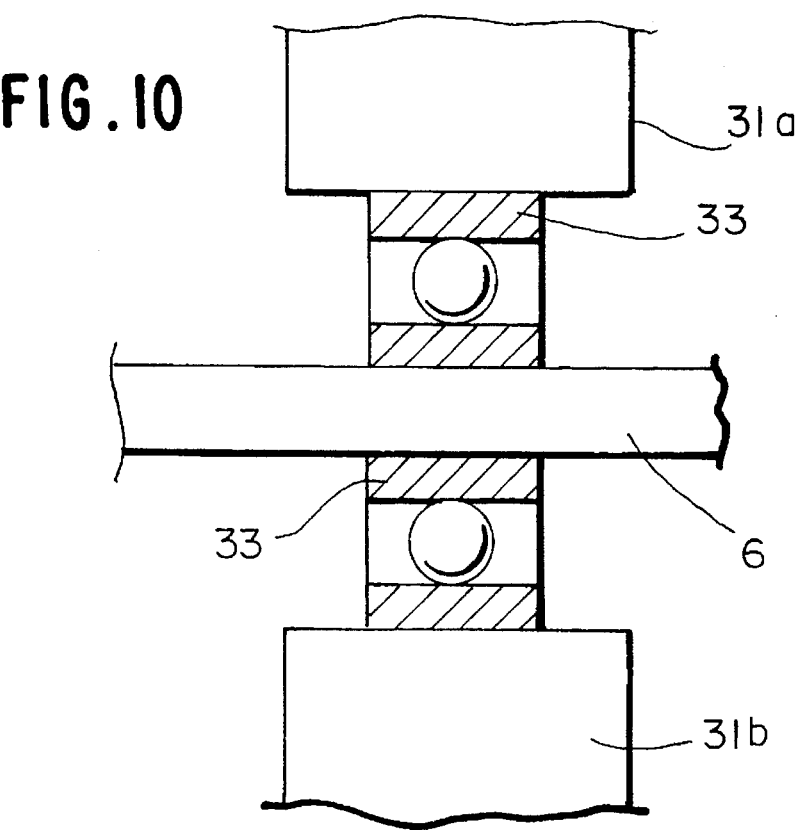
FIG. 10 is a cross-sectional view showing a bearing portion of the inversion type K-filter shown in FIG. 9.

FIG. 10 shows an example of the bearing portion in which a ball bearing 33 is used. As to the bearing, various known techniques, such as rolling-element bearings, plain bearings and the like may be used.

Figure 11:
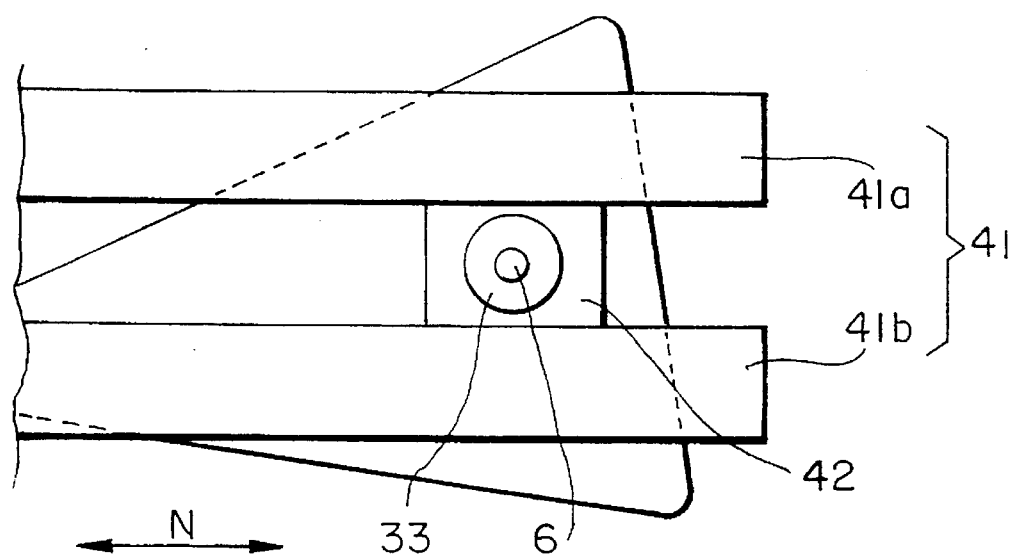
FIG. 11 is a diagrammatic view showing an inversion type K-filter according to yet another embodiment of the present invention.

FIG. 11 illustrates another embodiment in which the K-containers 5a, 5b are detachably mounted on a supporting member 41. In this embodiment, there is a bearing support member 42 disposed between upper and lower plate members 41a, 41b for supporting thereon each support shaft 6 and a corresponding bearing 33 such that the support shaft 6 of the K-container 5a, 5b is held rotatable within the bearing support member 42 via the bearing 33.

With this arrangement, the bearing support members 42 are displaced in the direction of the arrow N to change the extent of the X-ray permeable region 2 defined between two K-containers 5a, 5b (only one being shown) to cope with the size and the like condition of the object H to be examined, in the same manner as done in the embodiment of FIG. 10. Furthermore, it is also possible to displace the bearing support members 42 of only one K-container 5a, 5b to place the K-containers 5a, 5b in a distorted position relative to the supporting member 41, thus making it possible to deal with the examination of an object composed of a particular organ.

The K-containers 5a, 5b may be constructed as being detachable relative to the supporting member 1a in a manner other than specifically described above. For example, the supporting member 1a in the embodiment shown in FIGS.

2–5 may be composed of two parts which can be separated along a common plane including axes of the bearing portions for a purpose of attachment and detachment of the K-containers 5a, 5b.

At least one of the support shafts 6 of each K-container 5a, 5b may be composed of, or coupled with, the output shaft of a position control motor composed, for example, of a stepping motor, In this case, operation of the stepping motor is controlled in synchronism with the rotation of the serial high-speed rotatograph apparatus to ensure an optimal adjustment of the position of the K-containers with respect to the angular position of the serial high-speed rotatograph apparatus.

It is preferable that the support shafts 6 of the two K-containers 5a, 5b are independently rotatable by the corresponding stepping motors to adjust the respective positions of the K-containers 5a, 5b to meet various requirements determined by conditions of an object to be examined. By virtue of this independent movement, the two K-containers 5a, 5b are allowed to move asymmetrically with the result that the K-filter 1 is able to conduct optimal filtering with respect to any sort of object.

In the embodiments described above, the rotation accompanied by the photographing is continuous. However, the X-ray tube device 12, the X-ray television camera 14 and so on which constitute the serial high-speed rotatograph apparatus 10 may be constructed in such a manner that pulsed radiation is emitted selectively at predetermined intervals of a unit angle or at predetermined intervals of time.

The serial high-speed rotatograph apparatus 10 is designed to rotate to 180° in 5 sec or less, or to 360° in 10 sec or less. In place of the emission of pulsed radiation (X-ray) executed depending on the rotation angle, the serial high-speed rotatograph apparatus 10 may undertake time-dependent emission of the pulsed X-ray for 2 to 4 sec which is achieved, under the control of a suitable switching device (not shown), at predetermined intervals of time corresponding to the aforesaid predetermined angular intervals while the rotatograph apparatus is held immovable or stationary.

Stated more specifically, the serial high-speed rotatograph apparatus 10 is stopped at a fixed position under the control of the rotation controller 15, and then the time-dependent emission of the pulsed X-ray is effected under the control of the non-illustrated switching device in the rotation controller 15 so as to conduct continuous photographing.

In this instance, the intervals of the pulsed X-ray emission are the same as those effected in high-speed rotation at the rate of about 5 sec/180°–about 10 sec/360°. Other structural details may be the same as those in the embodiment previously described.

With this construction, continuously rotating images and serial images at a predetermined position can be obtained with respect to the same object through a single run of the photography with the result that the serial images at the predetermined position and the continuously rotating images are observed in the same and series state.

The rotation photographing time (θ sec) of the serial high-speed rotatograph apparatus 10 is determined by the angle for observing one heartbeat, the rotation angle, and the heart rate of the object.

This means that to determined the rotation photographing time (θ sec) of the serial high-speed rotatograph apparatus 10, the one-heartbeat observation angle (δ°) and the rotation angle (SR°) are determined previously and inputted from the keyboard 20 via the control interface 19 into the CPU 22. On the other hand, the number of heartbeats per minute, i.e., the heart rate (η) is automatically inputted from the synchronous electrocardiograph 21 via the control interface 19 into the CPU 22. Then, the CPU 22 computes the rotation photographing time based on the one-heartbeat observation angle, the rotation angle, and the heart rate of the object. Thus, operation of the rotatograph apparatus 10 can be controlled at a rotational speed corresponding to the computed rotation photographing time. Subsequently, the pulsed of X-ray emission and the signal acquisition achieved at each unit angle will be continued over the entire 360°.

Injection of the X-ray contrast medium (X-ray impermeable fluid substance) 4 and X-ray exposure are commenced such that the X-ray contrast medium 4 injection follows the X-ray exposure with a delay, and vice versa. The rotational speed is set in the range of about 5 sec/180° to about 10 sec/360° for achieving high-speed rotation, and in the illustrated embodiment, the number of frames to be exposed is set in the range of 144 frames per 180°, i.e., 288 frames per 360°.

Figure 12:
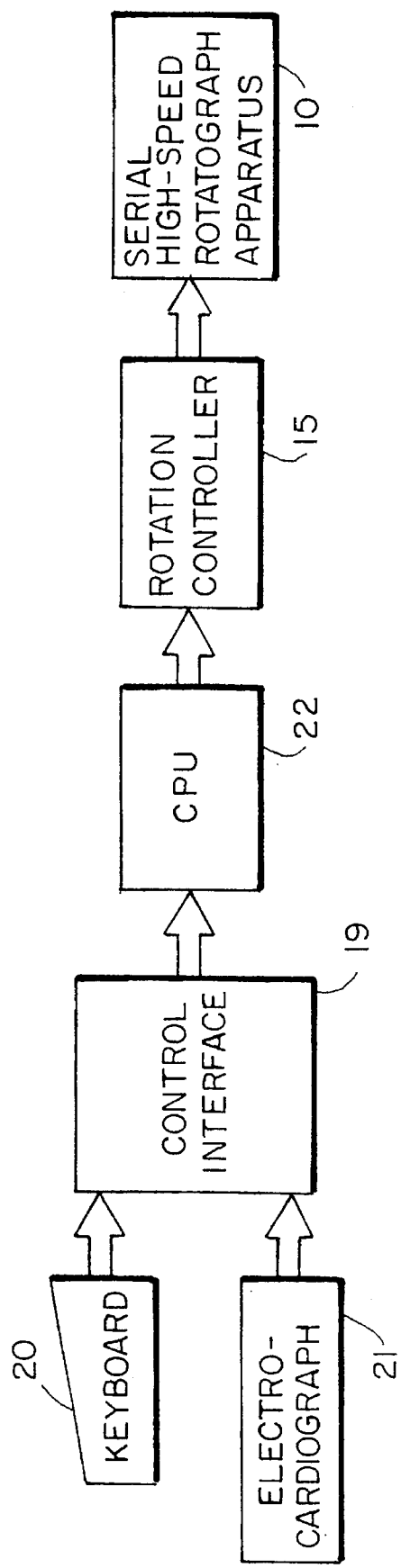
FIG. 12 is a block diagram showing the control of the serial high-speed rotatograph apparatus.

As will become apparent from a description given below with reference to FIGS. 1 and 12, a predetermined one-heartbeat observation angle (δ°) and a predetermined rotation angle (SR°) are inputted from the keyboard 20 via the control interface 19 into the CPU 22.

At the same time, from the synchronous electrocardiograph 21 connected to an object H to be examined, a heart rate (η), i.e., the number of heartbeats per one minute is automatically inputted via the control interface 19 into the CPU 22.

Thus inputted heart rate (η), one-heartbeat observation angle (δ°) and rotation angle (SR°) are used in an arithmetic operation performed by the CPU 22 to determine the rotation photographing time (θ sec) which is given by the following equation:

$$\theta(\text{sec}) = SR° \times 60/(\eta \times \delta°)$$

A rotational speed corresponding to the thus calculated rotation photographing time (θ) is sent to the rotation controller 15 which controls the drive of the high-speed rotation device (not shown) and sets respective rotation speeds for the high-speed rotation device and the rotating stage T which constitute the serial high-speed rotatograph apparatus 10.

When a main switch (not shown) is turned on, the serial high-speed rotatograph apparatus 10 starts photographing an image at each unit angle of the object H about the axis of the object H based on the rotation photographing time.

In the embodiment described above, the number of heartbeats per minute (η) is inputted from the synchronous electrocardiograph 21 connected to the object H. Alternative, it is possible to input the number of heartbeats per second (η') in which instance the rotation photographing time (θ sec) can be obtained and given by:

$$\theta = SR° \times 1/(\eta' \times \delta°)$$

Based on the rotation photographing time, the X-ray tube device 12 and a combined unit of the image intensifier 13 and X-ray television camera 14 disposed in diametrically opposed relation are angularly moved or turned about the axis of the object H at a high speed from a predetermined angular position. During that time, a high voltage is applied from the X-ray high-voltage generator 11 to the X-ray tube device 12 in synchronism with a vertical synchronizing signal of the X-ray television camera 14. Thus, photographing is conducted at a rotation photographing time well matched with the heart rate supplied from the synchronous electrocardiograph 21.

For instance, when the heart rate (η) of the object H is 120, if the one-heartbeat observation angle (δ°) and the rotation angle (SR°) are 30° and 360°, respectively, the rotation photographing time (θ) will be 6 sec. This means that rotation photographing over 360° in 6 sec is sufficient to produce images extremely useful for diagnostic examination. In the event of observation over 180°, the rotation photographing time will be 3 sec.

Thus, as long as the one-heartbeat observation angle (δ°) and the rotation angle (SR°) are determined by a viewer or observer in view of a physical illness or defect and an object (organ to be examined) H, the heart rate of the object H is automatically inputted from the synchronous electrocardiograph to set an appropriate rotation photographing time for controlling the serial high-speed rotatograph apparatus 10 via the rotation controller 15.

The serial high-speed rotatograph apparatus 10 is so constructed as to perform reverse photographing. Namely, within the aforesaid rotation photographing time, the apparatus is able to conduct reciprocating photographing several times within a predetermined angle of 60°, for example, and also conduct continuous photographing while it is rotating alternately in the forward and reverse directions over an angle of 180° or 360°.

The serial high-speed rotatograph apparatus 10 of the foregoing construction operates as follows. In FIG. 1, the keyboard 20 is operated to set various necessary photographing conditions. Then, the high-speed rotation device and the rotation controller 15 starts rotation of the serial high-speed rotatograph apparatus 10.

When the X-ray tube device 12 and the X-ray television camera 14 of the serial high-speed rotatograph apparatus 10 reach respective preset angular positions, a necessary amount of X-ray contrast medium 4 is injected at high speed from the automatic X-ray contrast medium injecting device AJ. Concurrently therewith, the X-ray pulses are emitted from the X-ray tube device 12, and signals are successively collected via the image intensifier 13 into the X-ray television camera 14.

The X-ray tube device 12 of the serial high-speed rotatograph apparatus 10 has attached thereto an inversion K-filter 1 having two K-containers 5a, 5b holding therein an X-ray impermeable fluid substance (X-ray contrast medium) 4.

Figure 7:
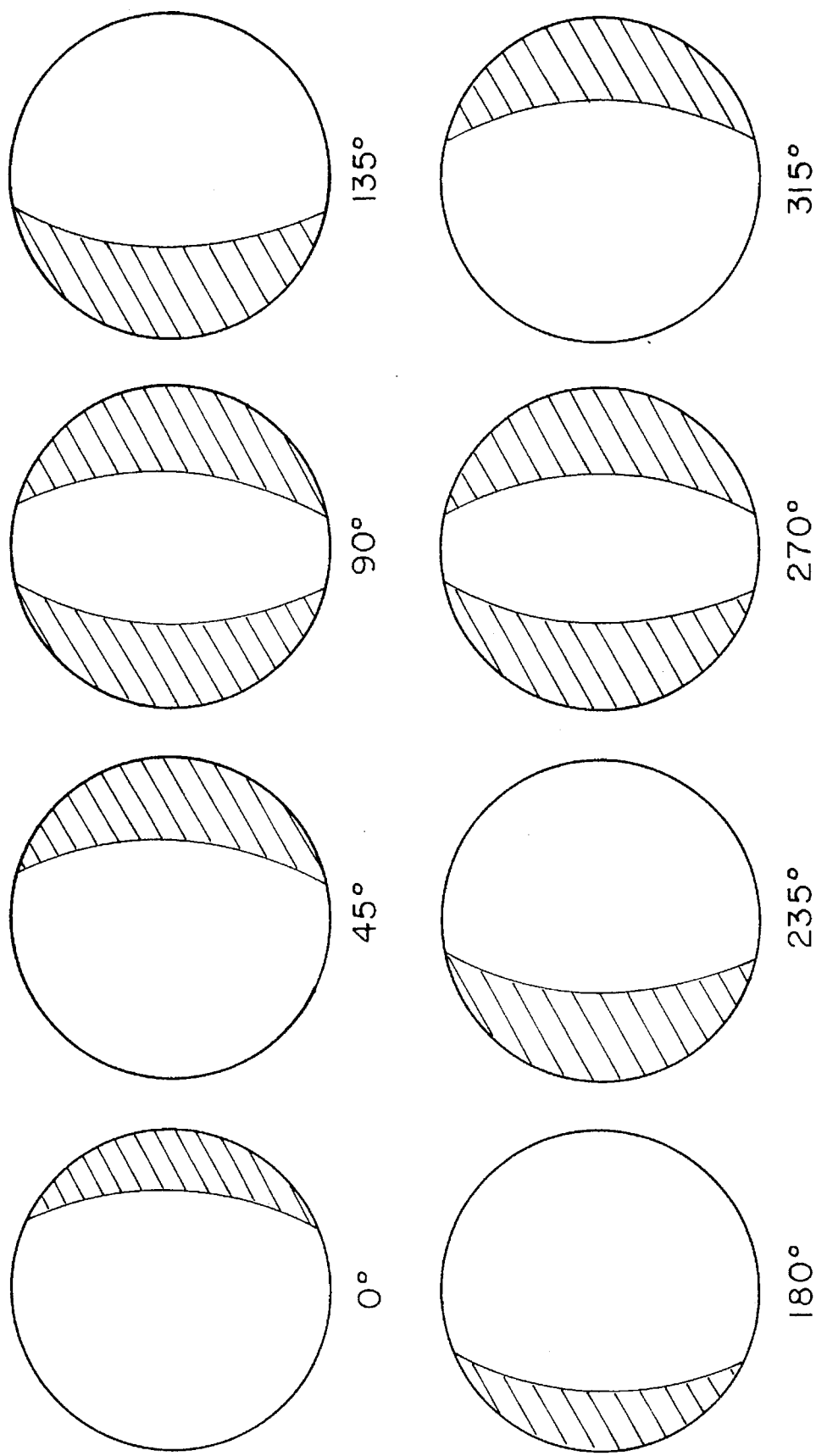
FIG. 7 is a view showing various images corresponding to different positions of the inversion type K-filter shown in FIG. 6.

Operation of the inversion K-filter 1 will be described below with reference to FIGS. 6 and 7. FIG. 6 diagrammatically shows an example of the serial high-speed rotatography performed in the clockwise direction, in which successive angular positions of the inversion K-filter 1 are spaced at intervals of 45°. FIG. 7 shows various photographing conditions corresponding to the respective angular positions of the inversion K-filter 1 shown in FIG. 6.

The object H to be examined by this serial high-speed rotatography is the chest of a human body, for example. As shown in FIG. 6, when the X-ray tube device 12 is located at the 0° position, the K-containers 5a, 5b are disposed in a vertical central position in the supporting member 1a. The X-ray impermeable fluid substance 4 in the K-container 5b moves in a position to compensate a front chest portion of the objects H, while the X-ray impermeable fluid substance (X-ray contrast medium) 4 in the K-container 5a moves in a region outside the X-ray exposure.

Namely, in this instance filtering is effected such that the exposed dose at a thin upper portion of the chest is limited by the K-filter 1, whereas the exposed dose at a thick lower portion of the chest is not limited by the K-filter 1. As a result, as designated at 0° in FIG. 7, only one side (right side in FIG. 7) is filtered.

In a range from 0° position to 180° position (upper side in FIG. 6), the K-containers 5a, 5b move to a lower position by their own weights, the weight of the X-ray impermeable fluid substance 4 and the like force. At the 45° position, the lower side of the object H is thicker than the upper side, so that the thin side (i.e., the upper side) of the object H is filtered. As a result, the one side (right side in FIG. 7) is filtered to a greater extent than at 0° position.

At the 90° position, the X-ray impermeable fluid substance 4 in the two K-containers 5a, 5b move in a position to compensate both lungs of the object H with the result that as designated by 90° in FIG. 7, the object H is irradiated with X-rays via the X-ray permeable region 2 disposed centrally between the two K-containers 5a, 5b.

At the 135° position, as opposed to at the 45° position, the X-ray impermeable fluid substance 4 in the K-container 5a changes its amount (effective amount pertaining to the filtering operation) to such an extent that the right lung is sufficiently compensated, while the X-ray impermeable fluid substance 4 in the K-container 5b rapidly moves to a position outside the X-ray exposure. Accordingly, filtering effected at this position is 180° out of phase or symmetrical with that attained at the 45° position.

At the 180° position, the K-containers 5a, 5b are disposed in a position 180° out of phase or symmetrical with the position assumed at the 0° position but they are disposed in a vertically central position of the supporting member 1a. Thus, the X-ray impermeable fluid substance 4 in the K-container 5a moves to a position to compensate the front chest of the object H, while the X-ray impermeable fluid substance 4 in the K-container 5b moves to a position outside the X-ray exposure.

In a range from the 180° position to 360° position, the K-containers 5a, 5b are turned (or apparently inverted), by the action of their own weights, the weight of the X-ray impermeable fluid substance 4 and the like force, about the support shafts 6 to that side of the supporting member 1 which is opposite to the side assigned to them in the 0°–180° angular range. At the 225° position, the thickness of the object H 4 is greater at its upper side than at its lower side, so that the thin side i.e., the upper side) is filtered.

At the 270° position, the position of the K-containers 5a, 5b is inverted in phase from that at the 90° position. However, like at the 90° position, the K-containers 5a, 5b are disposed in a position to compensate the both lungs, so that the object H is irradiated with the X-rays through the X-ray permeable region 2 located centrally between the K-containers 5a, 5b.

At the 315° position, as opposed to at the 225° position, the X-ray impermeable fluid substance 4 in the K-container 5a changes its amount (effective amount pertaining to the filtering operation) to such an extent that the left lung is sufficiently compensated, while the X-ray impermeable fluid substance 4 in the K-container 5b rapidly moves to a position outside the X-ray exposure.

As described above, the K-containers 5a, 5b are movable in a manner illustrated in FIG. 6 under the action of the gravitational force, centrifugal force and the like. Thus, in the range from 180° to 360° the K-containers 5a, 5b are able to perform the same role as they done in the range from 0° to 180°. Thus, at all angular positions, appropriate filtering can be attained.

The serial high-speed rotatograph apparatus 10 rotates about the object H while the latter is held stationary or immovable. During that time, the position and the amount of the X-ray impermeable fluid substance 4 in the K-containers 5a, 5b are variable with the angular position of the K-containers 5a, 5b, so that even when the object H has a vertical size unequal to the horizontal size, and in despite of rotation of the serial high-speed rotatograph apparatus 10, the amount of radiation penetrating the object H does not change abruptly even at a relatively thin or narrow portion of the object H, or at an air-containing organ such as lungs of the object H. Thus, an appropriate halation-compensation effect can always be obtained.

Thus, a local saturation (halation) on an image which is necessarily involved in the serial high-speed rotatography at each unit angle can be compensated.

In the case of the inversion K-filter 1 shown in FIGS. 2–5, the K-containers 5a, 5b are movable in the manner shown in FIG. 6 by the action of the gravitational force and the like, so that even in an angular range from 180° to 360°, they can do the same behavior as done in an angular range from 0° to 180°. Thus, a desired filtering function can be maintained at any position along the entire 360°. By using this inversion K-filter 1, it is possible to conduct spiral photographing, or multiple rotation photographing at the same portion.

Electric X-ray image signals obtained by the foregoing procedures are inputted via the logarithmic amplifier 16 to the A/D converter 18 which in turn converts the electric signals from an analog representation to a digital representation. The thus obtained digital image signals are then stored in individual fields of the frame memory 24. Subsequently, the digital signals are written in sequence from storage areas of the frame memory 24 into the display memory 25, and after being processed successively by the enhancer 26 and the D/A converter 27, serial or continuous rotating images are displayed frame-by-frame on the X-ray television monitor 28 according to the predetermined angular intervals.

In the continuous rotation display, the keyboard 20 or the like may be operated to change or repeat the selection of field direction in the storage fields (not shown) in the field memory 24, thereby displaying the reciprocating displays.

Thus, by properly operating the keyboard 20 and the like, the object H can be displayed in various known display modes, such as the continuous reciprocating display mode, the swing display mode in a predetermined angular range, etc. As to the display modes on the display device, such as reversal display mode, for example, suitable known techniques can be used.

Now, an example of the great vessel angiocardiography carried out by the above-described serial high-speed rotatograph apparatus 10 will be described. The circulation of great vessels constitute a system composed in sequence of: vena cavae-right atrium-right ventricle-pulmonary artery-pulmonary veins-left ventricle-left atrium-aorta-peripheral vessels-vena cavae.

The heart and great vessels are observed by the rotatography over a rotation angle of 360° and in a photographing time of 4 to 8 sec accompanied with injection of a 40 cc intravascular contrast medium into the right atrium. More particularly, if this observation is made under the conditions that the number of heartbeats per min, i.e., heart rate ($\eta$) is 120, the one-heartbeat observation angle ($\delta°$) is 30°, substitution of these values into the equation specified above gives that the rotation photographing time ($\theta$ sec) is 6 sec per 360°.

In this instance, in the circulatory system composed of vena cavae-right atrium-right ventricle-pulmonary artery-pulmonary veins-left atrium-left ventricle-aorta-peripheral vessels-vena cavae, rotatography begins from the right atrium into which the intravascular contrast medium is injected, and continues for 6 sec during which time a portion of the system including right ventricle-pulmonary artery-pulmonary veins-left atrium-left ventricle can be scanned.

Namely, the rotation photographing advances 60° per minute. In this instance, the intravascular contrast medium injected into the right atrium passes through the right atrium and the right ventricle in about 2 to 3 sec. However, since there are two heartbeats per second, it is possible to set the one-heartbeat observation angle in the range of 10° to 90°, preferably 30° to 50°, and more desirably 30° to 45°. With this one-heartbeat observation angle, clear photographing of the right atrium and the right ventricle is guaranteed, leading to reconstruction of images which are excellent and useful for diagnostic examination.

Furthermore, since the intravascular contrast medium leaving from the right ventricle will passes successively through the pulmonary artery, the pulmonary veins and the left atrium and flows into the left ventricle, and since the rotatography is conducted over the entire 360°, that portion of the heart and great vessel system including the left atrium and the left ventricle can also be scanned continuously, with the heart rate and the one-heartbeat observation angle held under the same condition as described above.

It is apparent from the foregoing description that the serial rotatography can be achieved in conformity with the heart rate and is able to get, over the entire 360°, excellent images useful for diagnostic examination. The photographing time of 4 to 8 sec is particularly advantageous for the cardiac and great vessel observations because the images obtained are extremely precise and appropriate for diagnostic examination.

This is also true when the rotatograph is applied in the angiography of an object H composed of a parenchymal or solid organ including carcinoma.

Hereinafter will be described of an example of the angiography which is applied to an object composed of a parenchymal or solid organ such, for example, as a carcinoma. The solid organs (i.e., those organs other than air-containing organs) form a system: arterial phase-parencymal phase (e.g., contrast staining of carcinoma)-venous phase. In the solid organ angiography, a contrast medium is injected into arterial system for imaging.

In this instance, if the rotation photographing time is set in the range of 6 to 8, the blood flow of the entire solid organ can be imaged by the serial rotatography achieved over the entire 360° even if the injection of the contrast medium is already completed when the contrast medium is transferred from the arterial phase to the solid phase in response to the heartbeat.

Like the angiocardiography previously described, in this solid organ angiography the observer sets a one-heartbeat observation angle ($\delta°$) and a rotation angle ($SR°$), so that when the number of heartbeats per unit time is automatically inputted from the synchronous electrocardiograph, an appropriate rotation photographing time is automatically determined and set.

The serial high-speed rotatograph apparatus 10 rotates about the object H while the letter is held stationary. During that time, the position and the amount of the X-ray impermeable fluid substance 4 in the K-containers 5a, 5b are variable with the angular position of the K-containers 5a, 5b, so that even when the object H has a vertical size unequal to the horizontal size, and in despite of rotation of the serial high-speed rotatograph apparatus 10, the amount of radiation penetrating the object H does not change abruptly even at a relatively thin or narrow portion of the object H, or at an air-containing organ such as lungs of the object H. Thus, an appropriate halation-compensation effect can always be obtained. Accordingly, a local saturation (halation) on an image which is necessarily involved in the serial high-speed rotatography at each unit angle can be compensated.

Electric X-ray image signals obtained by the foregoing procedures are inputted via the logarithmic amplifier 16 to the A/D converter 18 which in turn converts the electric signals from an analog representation to a digital representation. The thus obtained digital image signals are then stored in individual fields of the frame memory 24. Subsequently, the digital signals are written in sequence from storage areas of the frame memory 24 into the display memory 25, and after being processed successively by the enhancer 26 and the D/A converter 27, serial or continuous rotating images are displayed frame-by-frame on the X-ray television monitor 28 according to the predetermined angular intervals.

In the continuous rotation display, the keyboard 20 or the like may be operated to change or repeat the selection of field direction in the storage fields (not shown) in the field memory 24, thereby displaying the reciprocating displays.

Thus, by properly operating the keyboard 20 and the like, the object H can be displayed in various known display modes, such as the continuous reciprocating display mode, the swing display mode in a predetermined angular range, etc. As to the display modes on the display device, such as reversal display mode, for example, suitable known techniques can be used.

As described above, images of the object H taken by the serial rotatography are displaced on the X-ray television monitor (CRT) 28. Since these images are rotatographic images taken concentrically about the object H, the distance between the X-ray tube device 12 and the object H to be scanned, and the distance between the object H and the combined unit of the image intensifier 13 and the X-ray television camera 14 serving as an image sensor are always constant throughout the images taken from different angles.

Thus, by the serial high-speed rotatograph apparatus 10, successive images are taken one at each of the unit angles starting from a given angular position (i.e., arbitrary angle) and arrayed in the circumferential direction about the axis of an object H. The successive images taken on the unit-angle basis are converted into digital pulses by the single A/D converter 18 which reads electric image signals through the progressive readout method.

The digitized images are recorded in the high-speed dynamic RAM (D-RAM) 30 and displayed in sequence on the single X-ray television monitor 28 as serial two-dimensional (2-D) planar images taken at respective unit angles.

These parts of the D-RAM 30 which function as the file memory 23, the frame memory 24 and the display memory 25 are disposed in parallel on a single bus B which is connected to the CPU 22 as described above. The entire system described above is controlled by the CPU 22 according to commands supplied from the keyboard 20, a mouse and the like.

The above-described photographing method may correspondingly apply to the selective angiography of the head, thoracic and abdominal aortic branches, and for angiography of upper and lower extremities and intrapelvic organs. In these examinations, however, the angular velocity should not always be set depending on the heart rate but may be set arbitrarily in the range of 3 to 10 sec per 360°.

Figure 13:
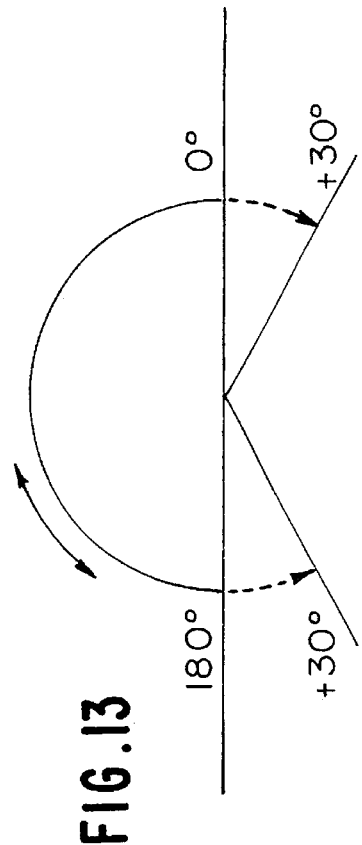
FIG. 13 is a diagrammatic view showing a range of rotation of a photographing device.

In the embodiments described above, the high-speed rotation device is rotatable to more than 360°. However, a similar device having a rotatable range of 180° can also be used, in which instance the range of rotatography is set such that reverse photographing (swing photographing) through or within an angle of 180° is achievable, as indicated by solid line shown in FIG. 13.

In addition, the above-described inversion K-filter can conduct filtering at any angular position in 360°. This means that a sufficient filtering effect is attainable even when the scanning begins with rotatograph apparatus disposed in a position 90° out of phase with the horizontal. Accordingly, the K-filter can be used with the conventional photographing apparatus, and is also suitable for use with the C-shaped arm type apparatus.

With this reverse or swing mode of photographing, it is possible to conduct reverse or reciprocating displaying without using the conventional swing mode relying on a complicated image processing, not in the form of reciprocating display of the same image but in the form of continual reciprocating display of live images.

Preferably, a rotatable region of about 30° is added to each end of the 180° range of rotatography, thus ensuring that the high-speed rotation device can rotate the serial high-speed rotatograph apparatus 10 at the desired speed through the angular photographing region. This arrangement is particularly advantageous for the operation of the high-speed rotation device when the reverse or reciprocating photographing is to be achieved where the direction of rotation of the serial high-speed rotatograph apparatus 10 should be reversed.

Although the embodiments described above are directed to the angiography using radiation in the form of the X-rays, the invention should by no means be limited to the disclosed angiography, but may be applied in any other medical radiography, such as the sialography, bronchography, myelography, cystography, pyelography, hysterosalpingography, etc. In the embodiment previously described, the serial high-speed rotatograph apparatus is rotated about a longitudinal or major axis of the object, however, rotation about a transverse or minor axis of the object is of course possible.

Capability of Exploitation in Industry:

As described above, the filter according to the invention is particularly effective to prevent halation when used in a serial high-speed rotatograph apparatus using radiation represented by the X-rays, is suitable for use with rotatograph apparatus having a scanning angle more than 180°, such as CT scanners, and is also effective to prevent halation in any other apparatus than the medical apparatus. The serial high-speed rotatograph apparatus of this invention is able to perform serial high-speed rotatography by use of any form of radiation, is suitable not only for medical scanning but for the radiography requiring various the serial rotatography.

We claim:

1. A K-filter for serial high-speed rotatography and adapted to be attached to an apparatus for the serial high-speed rotatography for photographing an object to be examined by use of X-rays, said K-filter comprising two K-containers each defining a space fluidly containing therein a radiopaque fluid substance, and a radiotransparent region formed between said two K-containers, said K-containers being pivotally supported by a supporting member and being of the inversion type which allows the radiotransparent-region sides of the K-containers to move.

2. A K-filter for serial high-speed rotatography according to claim 1, wherein said supporting member is formed with a bearing portion, said K-containers each have a pivot shaft rotatably supported by said bearing portion, and as said radiopaque fluid substance in each of said K-containers moves by gravity, said K-container turns about said pivot shaft to angularly move its radiotransparent-region side.

3. A K-filter for serial high-speed rotatography according to claim 1 or 2, wherein said radiopaque fluid substance is filled in said K-containers to the extent of 10% to 50% of the capacity of the K-containers.

4. A K-filter for serial high-speed rotatography according to claim 1 or 2, wherein said K-containers each have opposite sides having the shape of an isosceles triangle.

5. A K-filter for serial high-speed rotatography according to claim 1 or 2, wherein the inside surface of at least said radiotransparent-region side of each of said K-containers is covered with a coating material.

6. A K-filter for serial high-speed rotatography according to claim 2, wherein said pivot shaft is adjusted in position by a position control motor in synchronism with rotation of the serial high-speed rotatograph apparatus.

7. A K-filter for serial high-speed rotatography according to claim 2, said bearing portion is displaceable relative to said supporting member.

8. A K-filter for serial high-speed rotatography according to any one of the preceding claim 1 or 2, wherein at least one of said K-containers is moved to render respective movements of the two K-containers asymmetric with each other.

9. The K-filter for serial high-speed rotatography according to claim 3, wherein at least one of said K-containers is moved to render respective movements of the two K-containers asymmetric with each other.

10. The K-filter for serial high-speed rotatography according to claim 4, wherein at least one of said K-containers is moved to render respective movements of the two K-containers asymmetric with each other.

11. The K-filter for serial high-speed rotatography according to claim 5, wherein at least one of said K-containers is moved to render respective movements of the two K-containers asymmetric with each other.

12. The K-filter for serial high-speed rotatography according to claim 6, wherein at least one of said K-containers is moved to render respective movements of the two K-containers asymmetric with each other.

13. The K-filter for serial high-speed rotatography according to claim 7, wherein at least one of said K-containers is moved to render respective movements of the two K-containers asymmetric with each other.

14. The K-filter for serial high-speed rotatography according to claim 1 or 2, wherein said K-containers are detachably mounted on said supporting member.

15. The K-filter for serial high-speed rotatography according to claim 6, wherein said K-containers are detachably mounted on said supporting member.

16. The K-filter for serial high-speed rotatography according to claim 7, wherein said K-containers are detachably mounted on said supporting member.

17. The K-filter for serial high-speed rotatography according to claim 8, wherein said K-containers are detachably mounted on said supporting member.

18. An apparatus for serial high-speed rotatography disposed concentric with an object to be examined and rotatable for photographing the object, said apparatus comprising a radiation tube device having attached thereto a K-filter which comprises two K-containers each defining a space fluidly containing therein a radiopaque fluid substance, and a radiotransparent region formed between said two K-containers, said K-containers being pivotally supported by a supporting member and being of the inversion type which allows the radiotransparent-region sides of the K-containers to move.

19. The apparatus for serial high-speed rotatography according to claim 18, wherein said supporting member is formed with a bearing portion, said K-containers each have a pivot shaft rotatably supported by said bearing portion, and as said radiopaque fluid substance in each of said K-containers moves by gravity, said K-container turns about said pivot shaft to angularly move its radiotransparent-region side.

20. The K-filter for serial high-speed rotatography according to claim 18 or 19, wherein said containers are filled to 10% to 50% capacity with said radiopaque fluid substance.

21. The K-filter for serial high-speed rotatography according to claim 18 or 19, wherein said K-containers each have opposite sides having the shape of an isosceles triangle.

22. The apparatus for serial high-speed rotatography according to claim 18 or 19, wherein the inside surface of at least said radiotransparent-region side of each of said K-containers is covered with a coating material.

23. The apparatus for serial high-speed rotatography according to claim 19, wherein said pivot shaft is adjusted in position by a position control motor in synchronism with rotation of the serial high-speed rotatography apparatus.

24. The apparatus for serial high-speed rotatography according to claim 19, wherein said bearing portion is displaceable relative to said supporting member.

25. The apparatus for serial high-speed rotatography according to claim 18 or 19, wherein at least one of said K-containers is moved to render respective movements of the two K-containers asymmetric with each other.

26. The apparatus for serial high-speed rotatography according to claim 18, wherein said radiation tube device being so constructed as to emit pulsed exposure of radiation selectively at predetermined intervals of a unit angle and at predetermined intervals of time.

27. The apparatus for serial high-speed rotatography according to claim 26, wherein said supporting member is formed with a bearing portion, said K-containers each have a pivot shaft rotatably supported by said bearing portion, and as said radiopaque fluid substance in each of said K-containers moves by gravity, said K-container turns about said pivot shaft to angularly move its radiotransparent-region side.

28. The apparatus for serial high-speed rotatography according to claim 26 or 27 wherein said K-containers are filled to 10% to 50% capacity with said radiopaque fluid substance.

29. The apparatus for serial high-speed rotatography according to claim 26 or 27, wherein said K-containers each have opposite sides having the shape of an isosceles triangle.

30. The apparatus for serial high-speed rotatography according to claim 26 or 27, wherein the inside surface of at least said radiotransparent-region side of each of said K-containers is covered with a coating material.

31. The apparatus for serial high-speed rotatography according to claim 27, wherein said pivot shaft is adjusted in position by a position control motor in synchronism with rotation of the serial high-speed rotatography apparatus.

32. The apparatus for serial high-speed rotatography according to claim 17, wherein said bearing portion is displaceable relative to said supporting member.

33. The apparatus for serial high-speed rotatography according to claim 26 or 27, wherein at least one of said K-containers is moved to render respective movements of the two K-containers asymmetric with each other.

34. An apparatus for serial high-speed rotatography according to claim 18, wherein said apparatus is rotatable to 180° in 5 seconds or less, or to 360° in 10 seconds or less, and said apparatus while at rest is capable of emitting pulsed exposure of radiation for 2 to 4 seconds at intervals of time which correspond to said predetermined intervals of a unit angle.

35. An apparatus for serial high-speed rotatography according to claim 34, wherein said radiation tube device being so constructed as to emit pulsed exposure of radiation selectively at predetermined intervals of a unit angle and at predetermined intervals of time.

36. An apparatus for serial high-speed rotatography according to claim 18, wherein said apparatus has a rotation photographing time which is determined by an angle for observing one heartbeat of the object, a rotation angle, and a heart rate of the object.

37. An apparatus for serial high speed rotatography according to claim 36, wherein said radiation tube device being so constructed as to emit pulsed exposure of radiation selectively at predetermined intervals of a unit angle and at predetermined intervals of time.

38. An apparatus for serial high-speed rotatography according to claim 18, wherein a predetermined range of one-heartbeat observation angle $\delta°$, a predetermined rotational angle $SR°$, and a predetermined heart rate from a synchronous electrocardiograph are input into an arithmetic unit to set a rotating speed corresponding to rotation photographing time, and a signal representing said rotating speed is sent to a rotation controller for controlling said apparatus, said rotation controller controlling the rotation photographing time.

39. An apparatus for serial high-speed rotatography according to claim 38, wherein said radiation tube device being so constructed as to emit pulsed exposure of radiation selectively at predetermined intervals of a unit angle and at predetermined intervals of time.

40. An apparatus for serial high-speed rotatography according to claim 18, wherein said apparatus has a rotation photographing time $\Theta$ in seconds which is obtained and given by the following equation:

$$\Theta = SR° \times t/(\eta \times \delta°)$$

wherein $SR°$ is the rotation angle, t is the unit time, $\eta$ is the number of heartbeats per unit time t, and $\delta°$ is the one-heartbeat observation angle.

41. An apparatus for serial high-speed rotatography according to claim 40, wherein said radiation tube device being so constructed as to emit pulsed exposure of radiation selectively at predetermined intervals of a unit angle and at predetermined intervals of time.

42. An apparatus for serial high-speed rotatography according to claim 18, wherein said apparatus is capable of conducting continuous photography while it is rotating to 180° or 360° alternately in the forward and reverse directions.

43. An apparatus for serial high-speed rotatography according to claim 42, wherein said radiation tube device being so constructed as to emit pulsed exposure of radiation selectively at predetermined intervals of a unit angle and at predetermined intervals of time.

44. An apparatus for serial high-speed rotatography according to claim 34, wherein said apparatus has a rotatable region extending contiguously from each end of said 180° when said rotating angle is 180°.

45. An apparatus for serial high-speed rotatography according to claim 44, wherein said radiation tube device being so constructed as to emit pulsed exposure of radiation selectively at predetermined intervals of a unit angle and at predetermined intervals of time.

46. An apparatus for serial high-speed rotatography according to claim 44, wherein said apparatus is capable of conducting continuous photography while it is rotating to 180° or 360° alternately in the forward and reverse directions.

47. An apparatus for serial high-speed rotatography according to claim 46, wherein said radiation tube device being so constructed as to emit pulsed exposure of radiation selectively at predetermined intervals of an unit angle and at predetermined intervals of time.

* * * * *